United States Patent
Schilling et al.

(10) Patent No.: US 10,604,722 B2
(45) Date of Patent: *Mar. 31, 2020

(54) CONCENTRATED, LOW-VISCOSITY RHAMNOLIPID COMPOSITIONS

(71) Applicant: Evonik Degussa GmbH, Essen (DE)

(72) Inventors: Martin Schilling, Bonn (DE); Jochen Kleinen, Heinsberg (DE); Josef Lorenz, Krefeld (DE); Hans Henning Wenk, Mülheim an der Ruhr (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/520,157

(22) PCT Filed: Nov. 9, 2015

(86) PCT No.: PCT/EP2015/076019
§ 371 (c)(1),
(2) Date: Apr. 19, 2017

(87) PCT Pub. No.: WO2016/078947
PCT Pub. Date: May 26, 2016

(65) Prior Publication Data
US 2017/0335238 A1 Nov. 23, 2017

(30) Foreign Application Priority Data
Nov. 19, 2014 (EP) ..................... 14193779

(51) Int. Cl.
| C11D 1/06 | (2006.01) |
| C11D 3/22 | (2006.01) |
| C07H 13/06 | (2006.01) |
| A61Q 19/10 | (2006.01) |
| A61Q 5/02 | (2006.01) |
| A61K 8/60 | (2006.01) |

(52) U.S. Cl.
CPC ............ *C11D 1/06* (2013.01); *A61K 8/60* (2013.01); *A61Q 5/02* (2013.01); *A61Q 19/10* (2013.01); *C07H 13/06* (2013.01); *C11D 3/221* (2013.01)

(58) Field of Classification Search
None
See application file for complete search history.

(56) References Cited

U.S. PATENT DOCUMENTS

| 5,656,747 A | 8/1997 | Mixich et al. |
| 7,985,722 B2 * | 7/2011 | DeSanto ............... A01N 43/16 510/160 |
| 9,243,212 B2 | 1/2016 | Kuppert et al. |
| 9,271,908 B2 | 3/2016 | Allef et al. |
| 9,351,485 B2 | 5/2016 | Giessler-Blank et al. |
| 9,434,755 B2 | 9/2016 | Schilling et al. |
| 2013/0130319 A1 | 5/2013 | Schaffer et al. |
| 2014/0296168 A1 | 10/2014 | Schilling et al. |
| 2016/0249604 A1 | 9/2016 | Giessler-Blank et al. |

FOREIGN PATENT DOCUMENTS

| DE | 4237334 A1 | 5/1994 | |
| DE | 102012221519 A1 | 5/2014 | |
| DE | 102013205756 A1 | 10/2014 | |
| EP | 0499434 A1 * | 8/1992 | ............... C11D 1/06 |
| EP | 2410039 A1 * | 1/2012 | ........... C11D 3/0036 |
| JP | S6377535 A | 4/1988 | |
| JP | 2014111595 A | 6/2014 | |
| TW | 201 009 080 | 3/2010 | |
| WO | 2006/96912 A1 | 9/2006 | |

OTHER PUBLICATIONS

Lovaglio, Roberta B., et al. "Rhamnolipid emulsifying activity and emulsion stability: pH rules." Colloids and Surfaces B: Biointerfaces 85.2 (2011): 301-305.*
Amani, Hossein, et al. "Production of microbial rhamnolipid by Pseudomonas aeruginosa MM1011 for ex situ enhanced oil recovery." Applied biochemistry and biotechnology 170.5 (2013): 1080-1093.*
European Search Report dated Jun. 5, 2015 in EP 14193779.7 (5 pages).
German language International Search Report dated Apr. 21, 2016 in PCT/EP2015/076019 (5 pages).
German language Written Opinion dated Apr. 21, 2016 in PCT/EP2015/076019 (10 pages).
International Search Report dated Apr. 21, 2016 in PCT/EP2015/076019 (2 pages).
Peggau et al., U.S. Appl. No. 15/509,685, filed Mar. 8, 2017.
Yutaka Ishigami et al., "Colloid chemical effect of polar head moieties of a rhamnolipid-type biosurfactant," Langmuir, Bd. 9, Nr. 7, copyright Jul. 1993, pp. 1634-1636 3 pages).
XP002792578, Chemical Abstracts Service, Columbus, OH, US, Suzuki et al., "Synthesis and fluorescence properties of amphipathic fluroescent dye derived from microbial biosurfactants" (2 pages).
XP002792579, Chemical Abstracts Service, Columbus, OH, US, Gama et al., "Preparation of rhamnolipid pyrene acyl esters as fluorescent probes" (2 pages).
Champion et al., "Electron Microscopy of Rhamnolipid (Biosurfactant) Morphology: Effects of pH, Cadmium, and Octadecane," copyright 1995, Journal of Colloid and Interface Science, vol. 170, pp. 569-574 (6 pages).

(Continued)

*Primary Examiner* — John Pak
*Assistant Examiner* — Daniel L Branson
(74) *Attorney, Agent, or Firm* — Nexsen Pruet PLLC; Philip P. McCann

(57) ABSTRACT

A rhamnolipid composition including 30% by weight to 70% by weight, of at least one rhamnolipid and 30% by weight to 70% by weight of water, where the percentages by weight refer to the total composition, wherein the pH of the composition at 25° C. is from 5.5 to 7.0. In addition to the foregoing rhamnolipid composition, also set forth is a method to make a solution of rhamnolipids; and salt of at least one rhamnolipid.

19 Claims, No Drawings

(56) References Cited

OTHER PUBLICATIONS

Ishigami et al., "Surface of Active Properties of Rhamnolipids as Microbial Biosurfactants," see English Abstract, copyright 1987, pp. 791-796 (6 pages).
Ishigami et al., "The pH-Sensitive Conversion of Molecular Aggregates of Rhamnolipid Biosurfactant," copyright 1987, The Chemical Society of Japan, Chemistry Letters, pp. 763-766 (4 pages).
Lebrón-Paler et al., "Determination of the Acid Dissociation Constant of the Biosurfactant Monorhamnolipid in Aqueous Solution by Potentiometric and Spectroscopic Methods," copyright 2006, Anal. Chem., vol. 78, pp. 7649-7658 (10 pages).
Lovaglio et al., "Rhamnolipid Emulsifying Activity and Emulsion Stability: pH Rules," copyright 2011, Colloids and Surfaces B: Biointerfaces, vol. 85, pp. 301-305 (5 pages).
Raza et al., "Surface Properties and Sub-Surface Aggregate Assimilation of Rhamnolipid Surfactants in Different Aqueous Systems," copyright 2010, Biotechnol. Lett., vol. 32, pp. 811-816 (6 pages).

\* cited by examiner

CONCENTRATED, LOW-VISCOSITY RHAMNOLIPID COMPOSITIONS

This application is a national stage application under 35 U.S.C. § 371 of International Application No. PCT/EP2015/076019 filed 9 Nov. 2015, which claims priority to European Application No. 14193779.7 filed 19 Sep. 2014, the disclosures of which are expressly incorporated herein by reference.

FIELD OF THE INVENTION

The invention provides concentrated rhamnolipid compositions and also methods for the preparation thereof.

BACKGROUND

Rhamnolipids are surface-active glycolipids and metabolic products of particular microorganisms. They have particular surfactant properties, such as strong foam formation, for example, and are of interest for a wide variety of technical applications. Rhamnolipids may be prepared using both wild strains and genetically modified microorganisms. Methods for the preparation by fermentation and work-up of rhamnolipids are described in detail in the prior art, thus, for example, in US20130130319.

Surfactants incorporated in cosmetic formulations (e.g. shampoos, hand cleansers), household cleaners and also dishwashing compositions must be present in liquid form at common processing temperatures in order to ensure processing via pipeline systems and pumps in the producer of such products. The viscosity should be low in this case in order to ensure a simple and reliable conveying. At the same time, the highest possible surfactant concentration is nevertheless desired here to allow preparation of environmentally-friendly formulations having low water content. At the same time, the drop in viscosity on dilution with water must be kept as low as possible since the formulated end products, such as shampoos, hand cleansers and detergents, for example, should have a sufficient viscosity so it can be handled better by the user. No rhamnolipid-containing compositions are known from the literature which correspond to these requirements.

The product forms known from the literature and available on the market are either solids which were isolated via various methods in more or less pure form (e.g. removal of a solvent by drying), pure products which are marketed in low and medium aqueous concentrations (e.g. up to 25% by weight) or are liquid products in which the main component(s) is/are vegetable oil or degradation products of vegetable oil originating from fermentation. These are therefore rhamnolipid solutions in an oil phase, and the corresponding products have the critical disadvantage that they only foam very poorly and are therefore uninteresting for actual surfactant applications.

A highly concentrated product form is also known from DE4237334A1, which may be obtained by a particularly simple method for purifying and concentrating rhamnolipids. In this case, the RL is precipitated from a fermentation broth by acidifying to pH=3 and the corresponding RL solid can be concentrated by centrifugation. In this case, solid suspensions or pastes are obtained having a high rhamnolipid solids content of 30 to 40% by weight and a very high viscosity. Abdel-Mawgoud et al. in Appl Biochem Biotechnol. 2009 May; 157(2):329-45 describe a similar method.

The solid dispersions thus obtained are unsuitable for further processing on a large industrial scale, for example, preparation of formulations for shampoos and household cleaners, since they are not suitable for conveying with typically used pumps owing to their high viscosity and their non-homogeneity.

DE102012221519A1 describes a method for obtaining rhamnolipids with excellent foaming properties, in which aqueous rhamnolipid solutions having a pH of 7 and a concentration of ca. 50% by weight are obtained. A disadvantage of this product form is the undesired, very sharp drop in viscosity on dilution. A further disadvantage is the reduced microbiological stability in the neutral state.

SUMMARY

The object of the invention was to provide compositions comprising highly concentrated and low-viscosity rhamnolipid. These should also have the lowest possible ionic strength and dilution with water should lead to the lowest possible changes in viscosity.

DETAILED DESCRIPTION

It has been found, surprisingly, that compositions comprising particularly highly concentrated and at the same time low-viscosity rhamnolipids could be obtained by a partial neutralization of a highly concentrated and highly viscous, acidic rhamnolipid solid suspension/paste. Surprisingly, these compositions show a lower drop in viscosity on dilution with water than completely neutralized compositions. Inorganic and organic bases may be used for the neutralization.

The present invention therefore provides aqueous compositions comprising high concentrations of rhamnolipids.

The invention further provides a method for preparing aqueous compositions comprising high concentrations of rhamnolipids.

An advantage of the present invention is that the ionic strength of the compositions comprising rhamnolipids can be kept low. As a result, appropriate flexibility in the subsequent adjustment of the pH and of the salt content of the final end formulation is left to the formulator.

A further advantage of the present invention is that the compositions have increased microbiological stability.

Another advantage of the present invention is that the compositions can be readily diluted.

A further advantage of the present invention is that the compositions can be thoroughly mixed with other surfactants.

Another advantage of the present invention is that the compositions enable the formulation of concentrated surfactant end formulations ("concentrates").

A further advantage of the present invention is that the compositions have a reduced foaming tendency on account of their high concentration and thus transport and conveying are simplified. Another advantage of the present invention is that the compositions allow simple incorporation of hydrophobic components such as oils, for example.

A further advantage of the present invention is that the compositions have high storage stability. Another advantage of the present invention is that the compositions do not go through extreme surges in viscosity on dilution with water.

A further advantage of the present invention is that the compositions cause lower contamination in pipelines during preparation and transport thereof and in addition enable a simpler cleaning. Another advantage of the present invention is that the transport of the compositions require a lower energy requirement for the transport.

A composition is claimed comprising
30% by weight to 70% by weight, preferably 35% by weight to 60% by weight, particularly preferably 40% by weight to 50% by weight, of at least one rhamnolipid and
30% by weight to 70% by weight, preferably 40% by weight to 65% by weight, particularly preferably 50% by weight to 60% by weight, of water,
where the percentages by weight refer to the total composition, characterized in that the pH of the composition at 25° C. is from 5.5 to <7.0, preferably from 5.6 to 6.2 and particularly preferably from 5.6 to 6.0.

The term "rhamnolipid" in the context of the present invention are rhamnolipids encompassing protonated forms and also particularly salts thereof.

The term "rhamnolipid" in the context of the present invention is understood to mean particularly mixtures of compounds of the general formula (I) and salts thereof,

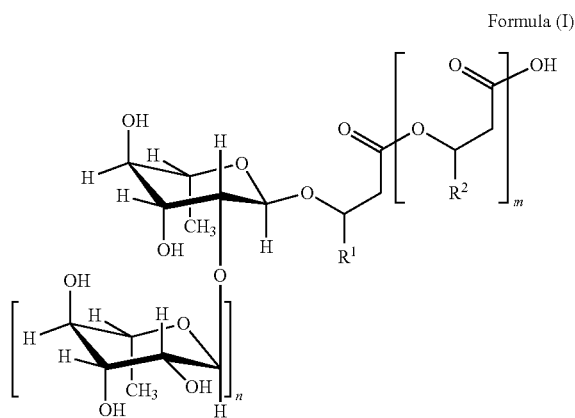

Formula (I)

where
m=2, 1 or 0,
n=1 or 0,
$R^1$ and $R^2$=mutually independently, identical or different, organic residues having 2 to 24, preferably 5 to 13 carbon atoms, in particular optionally branched, optionally substituted, particularly hydroxy-substituted, optionally unsaturated, in particular optionally mono-, bi- or tri-unsaturated alkyl residues, preferably those selected from the group consisting of pentenyl, heptenyl, nonenyl, undecenyl and tridecenyl and $(CH_2)_o$—$CH_3$ where o=1 to 23, preferably 4 to 12.

If n=1, the glycosidic bond between the two rhamnose units is preferably in the α-configuration. The optically active carbon atoms of the fatty acids are preferably present as R-enantiomers (e.g. (R)-3-{(R)-3-[2-O-(α-L-rhamnopyranosyl)-α-L-rhamnopyranosyl]oxydecanoyl}oxydecanoate).

The term "di-rhamnolipid" in the context of the present invention is understood to mean compounds of the general formula (I) or salts thereof, where n=1.

The term "mono-rhamnolipid" in the context of the present invention is understood to mean compounds of the general formula (I) or salts thereof, where n=0.

Distinct rhamnolipids are abbreviated according to the following nomenclature: "diRL-CXCY" are understood to mean di-rhamnolipids of the general formula (I), in which one of the residues $R^1$ and $R^2$=$(CH_2)_o$—$CH_3$ where o=X-4 and the remaining residue $R^1$ or $R^2$=$(CH_2)_o$—$CH_3$ where o=Y-4.

"monoRL-CXCY" are understood to mean mono-rhamnolipids of the general formula (I), in which one of the residues $R^1$ and $R^2$=$(CH_2)_o$—$CH_3$ where o=X-4 and the remaining residue $R^1$ or $R^2$=$(CH_2)_o$—$CH_3$ where o=Y-4.

The nomenclature used therefore does not distinguish between "CXCY" and "CYCX".

For rhamnolipids where m=0, monoRL-CX or diRL-CX is used accordingly.

If one of the abovementioned indices X and/or Y is provided with ":Z", this signifies that the respective residue $R^1$ and/or $R^2$ is equal to an unbranched, unsubstituted hydrocarbon residue having X-3 or Y-3 carbon atoms having Z double bonds.

The "pH" in connection with the present invention is defined as the value which is measured for the relevant composition at 25° C. after stirring for 5 minutes using a calibrated pH electrode in accordance with ISO 4319 (1977).

Unless otherwise stated, all percentages (%) given are percentages by weight.

To determine the content of rhamnolipids in the context of the present invention, only the mass of the rhamnolipid anion is considered, i.e. "general formula (I) less one hydrogen".

To determine the content of rhamnolipids in the context of the present invention, all rhamnolipids are converted by acidification into the protonated form (cf. general formula (I)) and quantified by HPLC.

The rhamnolipids present in the formulations according to the invention are present at least partially as salts on account of the given pH.

In preferred compositions according to the invention the cations of the rhamnolipid salts present are selected from the group comprising, preferably consisting of, $Li^+$, $Na^+$, $K^+$, $Mg^{2+}$, $Ca^{2+}$, $Al^{3+}$, $NH_4^+$, primary ammonium ions, secondary ammonium ions, tertiary ammonium ions and quaternary ammonium ions.

Exemplary representatives of suitable ammonium ions are tetramethylammonium, tetraethylammonium, tetrapropylammonium, tetrabutylammonium and [(2-hydroxyethyl)trimethylammonium] (choline) and also the cations of 2-aminoethanol (ethanolamine, MEA), diethanolamine (DEA), 2,2',2"-nitrilotriethanol (triethanolamine, TEA), 1-aminopropan-2-ol (monoisopropanolamine), ethylenediamine, diethylenetriamine, triethylenetetramine, tetraethylenepentamine, 1,4-diethylenediamine (piperazine), aminoethylpiperazine and aminoethylethanolamine.

The mixtures of the abovementioned cations may also be present as cations of the rhamnolipid salts present according to the invention.

Particularly preferred cations are selected from the group comprising, preferably consisting of, $Na^+$, $K^+$, $NH_4^+$ and the triethanolammonium cation.

The total amount of the abovementioned cations preferably account for 70% by weight to 99% by weight, particularly preferably 80% by weight to 90% by weight, of all cations present in the composition except $H^+$ and $H_3O^+$.

Preferred compositions according to the invention comprise 50% by weight to 99% by weight, preferably 70% by weight to 95% by weight, particularly preferably 85% by weight to 90% by weight, of rhamnolipid anions, where % by weight refers to all anions except $OH^-$ present in the composition.

In particularly preferred compositions according to the invention, the total dry mass comprises 40% by weight to 98% by weight, preferably 50% by weight to 95% by weight, particularly preferably 60% by weight to 90% by weight, of rhamnolipids, where the percentages by weight refer to the total dry mass.

The term "total dry mass" in the context of the present invention is understood to mean the portion of the composition according to the invention which remains—naturally in addition to water—after the composition according to the invention has been freed of the components which are liquid at 25° C. and 1 bar.

In compositions preferred according to the invention, at least 60% by weight, preferably at least 80% by weight, particularly preferably at least 95% by weight of the rhamnolipids are present in dissolved form, where the percentage by weight refers to the total amount of rhamnolipids.

This is measured by HPLC analysis of the total rhamnolipid before and after filtration through a 0.2 μm syringe filter, where the amount of rhamnolipids in the eluate corresponds to the amount of dissolved rhamnolipids.

It is preferred according to the invention that the compositions comprise 51% by weight to 95% by weight, preferably 70% by weight to 90% by weight, particularly preferably 75% by weight to 85% by weight, of diRL-C10C10, where the percentages by weight refer to the sum total of all rhamnolipids present.

It is preferred according to the invention that the compositions comprise 0.5% by weight to 9% by weight, preferably 0.5% by weight to 3% by weight, particularly preferably 0.5% by weight to 2% by weight, of monoRL-C10C10, where the percentages by weight refer to the sum total of all rhamnolipids present.

Preferred compositions according to the invention are characterized in that the weight ratio of all di-rhamnolipids present to all mono-rhamnolipids present is greater than 51:49, particularly greater than 91:9, preferably greater than 97:3, particularly preferably greater than 98:2.

It is preferred according to the invention that the compositions comprise 0.5 to 25% by weight, preferably 5% by weight to 15% by weight, particularly preferably 7% by weight to 12% by weight, of diRL-C10C12, where the percentages by weight refer to the sum total of all rhamnolipids present.

It is preferred according to the invention that the compositions comprise 0.1% by weight to 5% by weight, preferably 0.5% by weight to 3% by weight, particularly preferably 0.5% by weight to 2% by weight, of monoRL-C10C12 and/or, preferably and, 0.1% by weight to 5% by weight, preferably 0.5% by weight to 3% by weight, particularly preferably 0.5% by weight to 2% by weight, of monoRL-C10C12:1, where the percentages by weight refer to the sum total of all rhamnolipids present.

Particularly preferred compositions according to the invention are characterized in that they comprise
0.5% by weight to 15% by weight, preferably 3% by weight to 12% by weight, particularly preferably 5% by weight to 10% by weight, of diRL-C10C12:1,
0.5 to 25% by weight, preferably 5% by weight to 15% by weight, particularly preferably 7% by weight to 12% by weight, of diRL-C10C12,
0.1% by weight to 5% by weight, preferably 0.5% by weight to 3% by weight, particularly preferably 0.5% by weight to 2% by weight, of monoRL-C10C12 and
0.1% by weight to 5% by weight, preferably 0.5% by weight to 3% by weight, particularly preferably 0.5% by weight to 2% by weight, of monoRL-C10C12:1,
where the percentages by weight refer to the sum total of all rhamnolipids present.

It is moreover preferred if the composition according to the invention comprises only small amounts of rhamnolipids of the formula monoRL-CX or diRL-CX. In particular, the composition according to the invention preferably comprises
0% by weight to 5% by weight, preferably 0% by weight to 3% by weight, particularly preferably 0% by weight to 1% by weight, of diRLC10, where the percentages by weight refer to the sum total of all rhamnolipids present, and the term "0% by weight" is understood to mean no detectable amount.

It is preferred according to the invention that the compositions in accordance with the invention are essentially free from fatty oil (acylglycerols liquid at 20° C.) and therefore particularly comprise less than 0.5% by weight, in particular less than 0.1% by weight, particularly preferably no detectable amounts, of fatty oil based on the total composition.

The present invention further provides a method for preparing a solution of rhamnolipids comprising the steps of
a) providing a composition comprising
30% by weight to 70% by weight, preferably 35% by weight to 60% by weight, particularly preferably 40% by weight to 50% by weight, of at least one rhamnolipid, where the percentages by weight refer to the total composition, and having a pH at 25° C. of pH 1 to pH 5, preferably of pH 2.5 to 4.0, particularly preferably of pH 3.0 to pH 3.5,
b) adjusting the pH of the composition to pH 5.5 to pH<7.0, preferably to pH 5.6 to pH 6.2, particularly preferably to pH 5.6 to pH 6.0, and
c) adjusting the water content of the total composition to 30% by weight to 70% by weight, preferably 40% by weight to 65% by weight, particularly preferably 50% by weight to 60% by weight, of water
and adjusting the rhamnolipid content of the total composition to 30% by weight to 70% by weight, preferably 35% by weight to 60% by weight, particularly preferably 40% by weight to 50% by weight, of rhamnolipids,
where the percentages by weight refer to the total composition.

In particular, the compositions according to the invention can be prepared by the method according to the invention.

In accordance with the invention, the rhamnolipid in the composition provided in method step a) is present at least partially dispersed.

The term "present dispersed" in the context of the present invention is understood to mean that visually or light microscopically identifiable rhamnolipid aggregates are present, which sediment in the Earth's gravitational field to 10% by weight of rhamnolipid on dilution with water while maintaining the pH.

In particular, compositions are provided in method step a) which have a viscosity of 3 to 15, preferably 5 to 10, particularly preferably 6 to 8 Pas, measured in a rheometer at a shear rate of $10 \ s^{-1}$.

A method preferred according to the invention is characterized in that the pH is adjusted in method step b) by adding an organic or inorganic base, preferably in concentrated form.

The term "base in concentrated form" in the context of the present invention is understood to mean that the base is added in the form of a composition comprising at least 60% by weight, in particular at least 80% by weight of base, where the percentages by weight refer to the total composition added.

In the method according to the invention, preference is given to using bases selected from the group comprising, preferably consisting of, alkali metal and alkaline earth metal hydroxides such as NaOH, KOH, Mg(OH)$_2$, Ca(OH)$_2$; Al(OH)$_3$, NH$_4$OH, primary amines, secondary amines, tertiary amines and quaternary amines.

Exemplary representatives of suitable amines are 2-aminoethanol (also ethanolamine, MEA), diethanolamine (also DEA), 2,2',2''-nitrilotriethanol (also triethanolamine, TEA), 1-aminopropan-2-ol (also monoisopropanolamine), [(2-hydroxyethyl)trimethylammonium] (also choline) ethylenediamine, diethylenetriamine, triethylenetetramine, tetraethylenepentamine, 1,4-diethylenediamine (also piperazine), aminoethylpiperazine, aminoethylethanolamine, tetramethylammonium hydroxide, tetraethylammonium hydroxide, tetrapropylammonium hydroxide, tetrabutylammonium hydroxide, wherein preference is given to using 2-aminoethanol (also ethanolamine, MEA), diethanolamine (also DEA), 2,2',2''-nitrilotriethanol (also triethanolamine, TEA), 1-aminopropan-2-ol (also monoisopropanolamine) and (2-hydroxyethyl)trimethylammonium (also choline).

Particularly preferred bases are NaOH, KOH, NH$_3$, NH$_4$OH and triethanolamine.

It is also possible to use mixtures of the abovementioned bases in accordance with the invention.

If highly viscous pastes comprising rhamnolipids are provided in method step a) in the method according to the invention, mixing apparatus such as extruders, for example, can advantageously be used in method step b) and/or c).

Novel salts of rhamnolipids may be isolated from the formulations according to the invention and the solutions obtainable by the method according to the invention, for example, by removal of water.

The present invention furthermore provides, therefore, salts of at least one rhamnolipid, characterized in that it comprises at least one cation selected from the group comprising, preferably consisting of, Li$^+$, K$^+$, Mg$^{2+}$, Ca$^{2+}$, Al$^{3+}$, NH$_4^+$, primary ammonium ions, secondary ammonium ions, tertiary ammonium ions and quaternary ammonium ions.

The salts according to the invention preferably comprise at least 50% by weight, preferably at least 70% by weight, particularly preferably at least 95% by weight of the at least one cation, where the percentages by weight arise from the weight of the total salt "rhamnolipid anion plus cation" and refer to the total salt.

Exemplary representatives of suitable ammonium ions are tetramethylammonium, tetraethylammonium, tetrapropylammonium, tetrabutylammonium and [(2-hydroxyethyl)trimethylammonium] (choline) and also the cations of 2-aminoethanol (ethanolamine, MEA), diethanolamine (DEA), 2,2',2''-nitrilotriethanol (triethanolamine, TEA), 1-aminopropan-2-ol (monoisopropanolamine), ethylenediamine, diethylenetriamine, triethylenetetramine, tetraethylenepentamine, 1,4-diethylenediamine (piperazine), aminoethylpiperazine and aminoethylethanolamine.

Particularly preferred cations are selected from the group comprising, preferably consisting of, Li$^+$, Al$^{3+}$, NH$_4^+$ and the triethanolammonium cation.

With respect to their rhamnolipid composition with regard to mono-, di- and fatty acid content, preferred rhamnolipid salts according to the invention have the above cited preferred rhamnolipids present in the compositions according to the invention.

The present invention is illustratively described in the examples listed below without any intention of limiting the invention, whose scope is determined by the entire description and the claims, to the embodiments referred to in the examples.

EXAMPLES

Characterization of the Products
Quantification of Rhamnolipids by High Performance Liquid Chromatography (HPLC)

Quantification was conducted by HPLC. The acid form of the various rhamnolipid species was used as calibration standard in each case and the chromatographic separation was likewise carried out under acidic conditions. This leads to all RL components being quantified in one sample as the acid form.

For sample preparation, 1 ml of acetone was charged in a 2 ml reaction vessel using a positive displacement pipette (Combitip) and the reaction vessel immediately sealed to minimize evaporation. This was followed by the addition of 1 ml of rhamnolipid-containing sample which had been previously diluted as required. After vortexing, the mixture was centrifuged for 3 min at 13 000 rpm, and 800 µl of the supernatant transferred to an HPLC vial.

An Evaporative Light Scattering Detector (Sedex LT-ELSD Model 85LT) was used for detection and quantification of rhamnolipids. The actual measurement was carried out using Agilent Technologies 1200 Series (Santa Clara, Calif.) and a Zorbax SB-C8 Rapid Resolution column (4.6× 150 mm, 3.5 µm, Agilent). The injection volume was 5 µl and the method run time was 20 min. Aqueous 0.1% TFA (trifluoroacetic acid, solution A) and methanol (solution B) was used as mobile phase. The column temperature was 40° C. The ELSD (detector temperature 60° C.) and the DAD (diode array, 210 nm) serve as detectors. The gradient used in the method was:

| t [min] | Solution B % by volume | Flow rate [ml/min] |
|---|---|---|
| 0.00 | 70% | 1.00 |
| 15.00 | 100% | 1.00 |
| 15.01 | 70% | 1.00 |
| 20.00 | 70% | 1.00 |

Viscosity Measurements

The viscosity is measured using a rheometer (MCR 302, Anton Paar Germany) in a parallel plate measuring system. The upper plate had a diameter of 40 mm, the gap distance was 0.5 mm, measuring temperature was 25° C. The measurement was conducted in the shear rate range of 0.1-100 s$^{-1}$.

Example 1: Preparation of a Highly Concentrated RL Solution

A fermentation was carried out using a *Pseudomonas putida* strain pBBR1MCS2-Plac-rhlABC-T-Ptac-rhlC-T, the preparation of which is described in US2014296168, comprising the rhamnolipid biosynthesis genes RhlA, RhlB and RhlC. The preculture was carried out in a shaking flask as described in WO2012013554A1. For the main culture, a mineral medium (M9) was likewise employed. The fermentation was conducted in a 2 liter fermenter in a carbon-limited manner via a glucose feed input. The glucose feed input takes place by reference to the dissolved oxygen signal. The dissolved oxygen was regulated at 20% saturation via the stirrer speed. The pH is regulated to 7 via a pH electrode and addition of NH$_4$SO$_4$. To prevent excessive foaming of the fermentation broth, the defoamer DOW Corning 1500 was added as required. The fermentation was conducted over 4 days to a dry biomass of 15 g/l. The rhamnolipid concentration was determined by HPLC and was 9.8 g/l. After separating off the cells by means of centrifugation at 10 000 g, the fermentation broth was adjusted to a pH of 3.1 by adding concentrated $H_2SO_4$. By centrifugation again at 500 g, a paste-like solid concentrate was obtained with an RL fraction of 45% by weight and a viscosity of >10 000 mPas.

Example 2: Partial Neutralization with KOH

A 50% by weight aqueous KOH solution was added with continuous stirring to the paste-like suspension of the concentrated rhamnolipid precipitate (cf. previous example) and adjusted to a pH of 5.6. The paste-like mass liquefied at this point with an accompanying sharp drop in viscosity. A clear solution was from the suspension. 3 portions were removed from this solution and adjusted to pH=6, pH=7 and pH=8.5 respectively by addition of further KOH. After adjusting the pH of the solutions, these were adjusted to 50% by weight, 40% by weight, 30% by weight, 20% by weight and 10% by weight of rhamnolipid by addition of water and used for measurement of viscosity. The results are shown in table 1. It was found that it was possible to obtain an essentially liquid-thin but highly concentrated product by the partial neutralization. At the same time, a distinctly lower drop in viscosity occurred on dilution of the solutions at pH 5.6 and 6 than at pH 7 and 8.5.

TABLE 1

Viscosity (Pas, shear rate 10 1/s) of rhamnolipid compositions as a function of rhamnolipid concentration (% by weight) and pH. The formulations identified by * are inventive, since here the viscosity at high concentration is low and the drop in viscosity on dilution with water is likewise the lowest (compare the respective viscosities at 10% and 20%).

|        | 10%   | 20%   | 30%    | 40%    | 50%    |
|--------|-------|-------|--------|--------|--------|
| pH 3.5 | —     | —     | —      | 6.04   |        |
| pH 5.6 | 0.114 | 0.406 | 0.593* | 0.816* | 1.756* |
| pH 6.0 | 0.064 | 0.12  | 0.536* | 0.922* | 1.698* |
| pH 7.0 | 0.001 | 0.014 | 0.212  | 1.010  | 1.793  |
| pH 8.5 | 0.002 | 0.009 | 0.135  | 0.827  | 1.728  |

Example 3: Partial Neutralization with NaOH

The partial neutralization was carried out analogously to example 2, with the exception that a 50% by weight NaOH solution was used in place of KOH.

Example 4: Partial Neutralization with $NH_4OH$

The highly concentrated, acidic rhamnolipid suspension obtained in example 1 was adjusted by addition of water to a rhamnolipid content of 34.6% by weight, which had a pH of 3.18. 113 g of this suspension were removed and 3.64 g of a 25% by weight $NH_4OH$ solution were added with continuous stirring. The solution completely liquefied here and resulted in a pH of 5.63.

Example 5: Partial Neutralization with $Ca(OH)_2$ 2 g of $Ca(OH)_2$ were added to 101 g of an acidic rhamnolipid suspension comprising 34.6% by weight rhamnolipid and a pH of 3.18 and the resulting solid suspension was stirred at room temperature for 2 days. The solution completely liquefied here and resulted in a pH of 5.72.

Example 6: Partial Neutralization with $Mg(OH)_2$ 1.69 g of $Mg(OH)_2$ were added to 95 g of an acidic rhamnolipid suspension comprising 34.6% by weight rhamnolipid and a pH of 3.18 and the resulting solid suspension was stirred at room temperature overnight. The solution completely liquefied here and resulted in a pH of 6.06.

Example 7: Partial Neutralization with 2-Aminoethanol (MEA)

The fermentation and work-up of the rhamnolipids was carried out analogously to example 1 with the exception that the pH was only acidified to 3.8 in the precipitation step. The resulting rhamnolipid suspension was adjusted to a rhamnolipid content of 40% by weight by addition of water and divided into several portions of 50 g. 2.28 g of monoethanolamine (purity >99%) were then added to one of the portions under continuous stirring, which liquefied and clarified the solution. The pH of the resulting solution was 6.0.

Example 8: Partial Neutralization with Triethanolamine (TEA)

6.8 g of triethanolamine (purity >99%) were added to 50 g of a 40% by weight rhamnolipid suspension, pH 3.8 (cf. example 7) with continuous stirring. This liquefied and clarified the solution. The pH of the resulting solution was 6.2.

Example 9: Partial Neutralization with Monoisopropanolamine (MIPA)

2.76 g of MIPA (purity >99%) were added to 50 g of a 40% by weight rhamnolipid suspension, pH 3.8 (cf. example 7) with continuous stirring. This liquefied and clarified the solution. The pH of the resulting solution was 6.2.

Example 10: Partial Neutralization with Choline Hydroxide 9.4 g of choline hydroxide (46% by weight solution) were added to 50 g of a 40% by weight rhamnolipid suspension, pH 3.8 (cf. example 7) with continuous stirring. This liquefied and clarified the solution. The pH of the resulting solution was 6.2.

The invention claimed is:
1. A composition comprising
   from 30% by weight to 70% by weight, of a rhamnolipid and
   from 30% by weight to 70% by weight, of water,
   where the percentages by weight refer to the total composition, wherein the pH of the composition at 25° C. is from 5.5 to 6.2
wherein the rhamnolipid is a compound of the general formula (I) and salts thereof,

Formula (I)

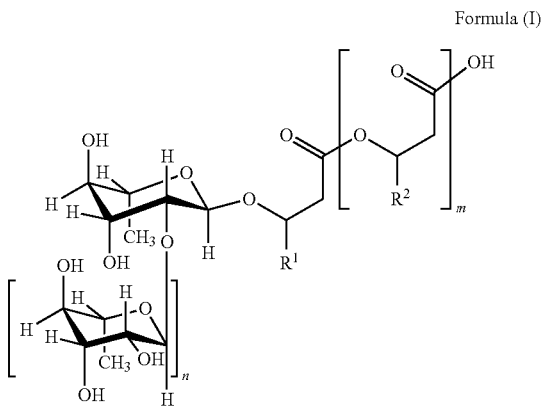

where
m=2, 1 or 0,
n=1 or 0,
$R^1$ and $R^2$=organic residues having from 2 to 24 carbon atoms
wherein the total dry mass comprises from 40% by weight to 98% by weight of the rhamnolipid,
where the percentages by weight refer to the total dry mass
wherein said composition comprises
from 3% by weight to 12% by weight of diRL-C10C12:1,
from 5 to 15% by weight of diRL-C10C12,
from 0.5% by weight to 3% by weight of monoRL-C10C12 and
from 0.5% by weight to 3% by weight of monoRL-C10C12:1,
where the percentages by weight refer to the sum total of all rhamnolipids present.

2. The composition according to claim 1, wherein the cations of the rhamnolipid salts present are selected from the group consisting of, $Li^+$, $Na^+$, $K^+$, $Mg^{2+}$, $Ca^{2+}$, $Al^{3+}$, $NH_4^+$, primary ammonium ions, secondary ammonium ions, tertiary ammonium ions or quaternary ammonium ions.

3. The composition according to claim 1, wherein said composition comprises
from 50% by weight to 99% by weight of rhamnolipid anions,
where % by weight refers to all anions except $OH^-$ present in the composition.

4. The composition according to claim 1, wherein said composition comprises
from 51% by weight to 95% by weight of diRL-C10C10,
where the percentages by weight refer to the sum total of all rhamnolipids present.

5. The composition according to claim 1, wherein said composition comprises
from 0.5% by weight to 9% by weight of monoRL-C10C10,
where the percentages by weight refer to the sum total of all rhamnolipids present.

6. The composition according to claim 1, wherein the weight ratio of all di-rhamnolipids present to all mono-rhamnolipids present is greater than 97:3.

7. The composition according to claim 1, wherein said composition comprises
from 0.5 to 25% by weight of diRL-C10C12,
where the percentages by weight refer to the sum total of all rhamnolipids present.

8. The composition according to claim 1, wherein said composition comprises
from 0.1% by weight to 5% by weight of monoRL-C10C12 and/or
from 0.1% by weight to 5% by weight of monoRL-C10C12:1,
where the percentages by weight refer to the sum total of all rhamnolipids present.

9. The composition according to claim 1, wherein said composition comprises
from 0% by weight to 5% by weight of diRLC10,
where the percentages by weight refer to the sum total of all rhamnolipids present.

10. A salt of at least one rhamnolipid according to claim 3, wherein said salt comprises at least one cation selected from the group consisting of, $Li^+$, $K^+$, $Mg^{2+}$, $Ca^{2+}$, $Al^{3+}$, $NH_4^+$, primary ammonium ions, secondary ammonium ions, tertiary ammonium ions and quaternary ammonium ions.

11. The composition according to claim 1, comprising from 35% by weight to 60% by weight, of at least one rhamnolipid and from 40% by weight to 65% by weight, of water,
where the percentages by weight refer to the total composition, wherein the pH of the composition at 25° C. is from 5.6 to 6.0.

12. The composition according to claim 1, wherein the total dry mass comprises from 60% by weight to 90% by weight, of rhamnolipids, where the percentages by weight refer to the total dry mass.

13. The composition according to claim 4, wherein the cations of the rhamnolipid salts present are selected from the group consisting of, $Li^+$, $Na^+$, $K^+$, $Mg^{2+}$, $Ca^{2+}$, $Al^{3+}$, $NH_4^+$, primary ammonium ions, secondary ammonium ions, tertiary ammonium ions and quaternary ammonium ions.

14. The composition according to claim 1, wherein said composition comprises
from 70% by weight to 95% by weight of rhamnolipid anions, where % by weight refers to all anions except $OH^-$ present in the composition.

15. The composition according to claim 1, wherein said composition comprises
from 51% by weight to 95% by weight of diRL-C10C10,
where the percentages by weight refer to the sum total of all rhamnolipids present.

16. A composition comprising
from 30% by weight to 70% by weight, of a rhamnolipid and
from 30% by weight to 70% by weight, of water,
where the percentages by weight refer to the total composition, wherein the pH of the composition at 25° C. is from 5.5 to 6.2
wherein the rhamnolipid is a compound of the general formula (I) and salts thereof,

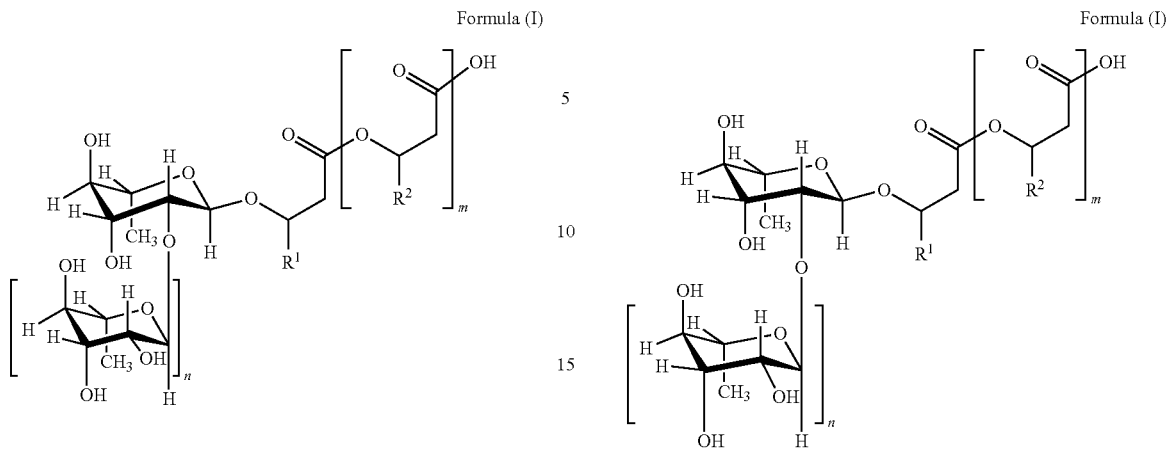

where
m=2, 1 or 0,
n=1 or 0,
R¹ and R²=organic residues having from 2 to 24 carbon atoms
wherein the total dry mass comprises from 40% by weight to 98% by weight of the rhamnolipid,
where the percentages by weight refer to the total dry mass
wherein said composition comprises
    from 5% by weight to 10% by weight of diRL-C10C12:1,
    from 7% to 12% by weight of diRL-C10C12,
    from 0.5% by weight to 2% by weight of monoRL-C10C12 and
    from 0.5% by weight to 2% by weight of monoRL-C10C12:1,
    where the percentages by weight refer to the sum total of all rhamnolipids present.

17. A method for preparing a solution of rhamnolipids comprising the steps of
    a) providing a composition comprising from 30% by weight to 70% by weight of a rhamnolipid, where the percentages by weight refer to the total composition, and having a pH at 25° C. of from 1.0 to 5.0, wherein the rhamnolipid is a compound of the general formula (I) and salts thereof, where
m=2, 1 or 0,
n=1 or 0,
R¹ and R²=organic residues having 2 to 24 carbon atoms
    b) adjusting the pH of the composition to 5.5 to 6.2 and
    c) adjusting the water content of the total composition to from 30% by weight to 70% by weight of water
and adjusting the rhamnolipid content of the total composition to from 30% by weight to 70% by weight of rhamnolipids wherein said composition comprises
    from 5% by weight to 10% by weight of diRL-C10C12:1,
    from 7% to 12% by weight of diRL-C10C12,
    from 0.5% by weight to 2% by weight of monoRL-C10C12 and
    from 0.5% by weight to 2% by weight of monoRL-C10C12:1,
    where the percentages by weight refer to the sum total of all rhamnolipids present.

18. The method according to claim 17, wherein the rhamnolipid in the composition provided in method step a) is present at least partially dispersed.

19. The method according to claim 17, wherein the pH is adjusted in method step b) by adding an organic or inorganic base, in concentrated form.

* * * * *